United States Patent [19]

Schreuder

[11] Patent Number: 4,721,705

[45] Date of Patent: Jan. 26, 1988

[54] SKIN TREATMENT COMPOSITIONS

[75] Inventor: Johannes C. P. Schreuder, Baarn, Netherlands

[73] Assignee: Chemish Adviesbureau Drs. J.C.P. Schreuder B.V., Netherlands

[21] Appl. No.: 652,831

[22] Filed: Sep. 20, 1984

[30] Foreign Application Priority Data

Sep. 26, 1983 [NL] Netherlands .................. 8303283

[51] Int. Cl.$^4$ .......................................... A61K 31/715
[52] U.S. Cl. ................................. 514/54; 514/513; 514/562; 514/629
[58] Field of Search ................ 514/513, 562, 54; 536/114, 26

[56] References Cited

U.S. PATENT DOCUMENTS 3,305,543 2/1967 Haskell ............................ 536/22
4,369,177 1/1983 Kozaki et al. ..................... 514/46

Primary Examiner—J. R. Brown
Assistant Examiner—Elli Peselev
Attorney, Agent, or Firm—Bierman and Muserlian

[57] ABSTRACT

Compositions for treating sun eczema or dyshydrosis of skin comprising (a) 0.1 to 5% by weight of panthenol, (b) 0.1 to 3% by weight of at least one member of the group consisting of methionine, N-acyl-cysteine and S-acyl-cysteine, said acyl being derived from an alkanoic acid of 1 to 7 carbon atoms, or cystine in an amount of at most 0.009% by weight, (c) 0.25 to 4% by weight of carraghenate, (d) 0.1 to 5% by weight of sodium chloride, (e) 0.1 to 2% by weight of a preservative and (f) sufficient water for 100% by weight, all weights based on the weight of the total composition and a method for treating sun eczema or dyshydrosis.

20 Claims, No Drawings

SKIN TREATMENT COMPOSITIONS

STATE OF THE ART

Sun eczema or dyshidrosis of the skin is indicated by the symptoms of sun vesicles, skin irritation and itching and various compositions have been proposed to treat these conditions. These compositions consisted of vaseline (paraffins), salicylic acid and 0.001% by weight of resorcine but the said compositions did not provide a rapid and sufficient treatment of the said symptoms. This could be due to the fact that the said compositions usually contained fat or fatty compounds which made the apparently disappeared symptoms reappear to a much worse degree after a necessarily long use of the compositions. Also, the frequent exposure of the skin to radiation, solaria, quick tanning systems, etc in which the skin is treated before such treatment with oil or fat containing creams for the promotion of the desired tanning of the skin and/or for protection against the specific radiation activity which accompanies the primary desired result is a major cause for such symptoms to a still greater degree.

OBJECTS OF THE INVENTION

It is an object of the invention to provide composition giving rapid and efficient treatment of sun eczema or dyshidrosis.

It is another object of the invention to provide an improved method for the treatment of sun eczema or dyshidrosis of skin.

These and other objects and advantages of the invention will become obvious from the following detailed description.

THE INVENTION

The novel compositions of the invention for treating sun eczema or dyshidrosis of skin are comprised of (a) 0.1 to 5% by weight of panthenol, (b) 0.1 to 3% by weight of at least one member of the group consisting of methionine, cysteine, N-acylcysteine and S-acyl-cysteine, said acyl being derived from an alkanoic acid of 1 to 7 carbon atoms, or cystine in an amount of at most 0.009% by weight, (c) 0.25 to 4% by weight of carraghenate, (d) 0.1 to 5% by weight of sodium chloride, (e) 0.1 to 2% by weight of a preservative and (f) sufficient water for 100% by weight, all weights based on the weight of the total composition.

In a preferred composition, the amount of panthenol is 1 to 2% by weight and the amount of sodium chloride is about 0.9% by weight.

The preferred amount of methionine is 1 to 2% by weight and the preferred amount of cysteine is at most 0.009% by weight. If a derivative of cysteine such as an N-acyl-cysteine like N-acetyl-cysteine or S-acyl-cysteine such as S-acetylcysteine is used, the preferred amount is 0.1 to 3%, more preferably 1 to 2%, by weight. Methionine is the preferred ingredient for the most attractive results. The cysteine or methionine component may be added as such as formed in situ by a spontaneous conversion by suitable means.

The carraghenate component is preferably a polysachcharide bearing sulfonic acid residues of a natural origin such as those derived from seaweed. The sulfonic acid residues optionally may have been esterified by glycol, propylene glycol and glycerine (so called modified carraghenates). Such carraghenates experimentally appear to effect a surprisingly attractive stabilizing effect of the total composition to be applied on the skin, and as an additional advantageous effect, the known attractive properties of such carraghenates such as elimination of an eventual hardening of sore tissue and the herewith connected curing without or with less extensive scars, as well as the advantageous healing effect and the complex forming properties with proteins, appear to be maintained in the final total system. The preferred amount of carraghenate is 1 to 2% by weight.

The amounts of carraghenate cause in the final composition the gel structure with a viscosity of from 1,000 to 5,000 centipoises, which is desired for an adequate application.

It will be appreciated by a person skilled in the art that the carraghenate may partially be replaced by alternative gel forming means such as carboxymethylcellulose, esterified polyacrylic acid such as Carbopol®, hydroxyethylcellulose in an amount which leads to a viscosity of the final composition in the same desired, hereinbefore mentioned specified range of 1,000 to 5,000 centiposises.

The preservative is preferably used in an amount of 0.3 to 1% by weight and may be any suitable preservative such as alkyl esters of p-hydroxy-benzoic acid, preferably methyl and/or propyl esters. A preferred preservative is a mixture of 0.1% of propyl p-hydroxy-benzoate and 0.2% by weight of methyl p-hydroxy-benzoate. Phenylglycol may be also used as the preservative alone or with said alkyl benzoates. More preferred are mixtures of phenylglycol and methyl and/or propyl and/or butyl p-hydroxybenzoates.

The compositions may also optionally contain other conventional additives such as 0.1 to 5%, preferably about 0.2%, by weight of perfume and/or 0.01 to 0.3%, preferably about 0.1%, by weight of an antioxidant.

The pH of the composition is preferably adjusted usted to 5 to 6 and more preferably to the pH range of 5.5 to 5.8 which is the normal pH of the outer skin layers.

As compared to the prior art compositions, the compositions of the invention show a fast and efficient activity accompanied with a rapid decrease in itching and a softening effect on the irradiated skin.

The compositions of the invention may be prepared by any suitable known means but preferably the panthenol, methionine and/or cysteine and/or cysteine derivative, sodium chloride and preservative are first dissolved in the aqueous phase and carraghenate is dissolved in the resulting solution.

The method of the invention for treating sun eczema or dyshidrosis of the skin of warm-blooded animals, including humans, comprises applying to afflicted skin an amount of a composition of the invention sufficient to relieve the symptoms of sun eczema or dyshidrosis. Preferably, the skin is first cleaned to remove oily or fatty compounds and the treatment is effected several times a day.

In the following examples there are described several preferred embodiments to illustrate the invention. However, it is to be understood that the invention is not intended to be limited to the specific embodiments.

EXAMPLE 1

A mixture of 5 g of panthenol, 5 g of methionine, 4 g of sodium chloride, 3 g of Phenonip (a preservative of phenylglycol), 0.05 g of an antioxidant and 1 g of a perfume solution were added with stirring to 471.95 g of distilled water and the mixture was stirred until dissolution was complete. Then, 10 g of carraghenate (Aubigum $X_2$) were added to the solution with stirring until there was complete dissolution.

EXAMPLE 2

A composition similar to Example 1 was prepared except 0.045 g of cysteine was used in placed of methionine and the Phenonip was replaced with 0.5 g of propyl p-hydroxy-benzoate and 1 g of methyl p-hydroxy-benzoate.

EXAMPLE 3

Using the procedure of Example 1, a composition was prepared consisting of 0.5% by weight of panthenol, 1% by weight of methionine, 0.90% by weight of sodium chloride, 0.75% by weight of Phenonip, 2% by weight of carraghenate and sufficient distilled water for the balance of the 100% composition.

EXAMPLE 4

Using the procedure of Example 1, a composition was prepared consisting of 1% by weight of panthenol, 1% by weight of methionine, 0.009% by weight of cysteine, 0.9% by weight of sodium chloride, 0.2% by weight of methyl p-hydroxy-benzoate, 0.1% by weight of propyl p-hydroxy-benzoate, 1.5% by weight of carraghenate and sufficient distilled water for the balance of the 100% composition.

EXAMPLE 5

Using the procedure of Example 1, a composition was prepared consisting of 1% by weight of panthenol, 2% by weight of methionine, 0.5% by weight of sodium chloride, 1% by weight of phenylglycol, 1.5% by weight of carraghenate and the balance being distilled water.

EXAMPLE 6

Using the procedure of Example 1, a composition was prepared consisting of 2% by weight of panthenol, 1% by weight of methionine, 1.2% by weight of sodium chloride, 0.4% by weight of phenylglycol, 0,1% by weight of methyl p-hydroxy-benzoate, 0.1% by weight of propyl p-hydroxy-benzoate, 1.2% by weight of carraghenate and the balance being distilled water.

EXAMPLE 7

Using the procedure of Example 1, a composition was prepared consisting of 1% by weight of panthenol, 1% by weight of methionine, 1% by weight of sodium chloride, 0.6% by weight of Phenonip, 0.01% by weight of preservative, 0.2% by weight of a perfume solution, 1.5% by weight of carraghenate and the balance being distilled water.

EXAMPLE 8

A person whose skin shows the symptoms of sun eczema has the skin throughly and carefully washed with soap and water and/or an alcoholic solution to remove the oily or fatty compounds from the skin. Then, 1 to 6 ml of the composition of Example 1 is spread evenly over the surface of the affected skin 3 to 6 times a day.

Various modifications of the compositions and method of the invention may be made without departing from the spirit or scope thereof and it should be understood that the invention is intended to be limited only as defined in the appended claims.

What I claim is:

1. A composition effective for treating sun eczema and dyshidrosis of skin comprising (a) 0.1 to 5% by weight of panthenol, (b) 0.1 to 3% by weight of at least one member of the group consisting of methionine, N-acyl-cysteine and S-acyl-cysteine, said acyl being derived from an alkanoic acid of 1 to 7 carbon atoms, or cystine in an amount of at most 0.009% by weight, (c) 0.25 to 4% by weight of carraghenate, (d) 0.1 to 5% by weight of sodium chloride, (e) 0.1 to 2% by weight of a preservative and (f) sufficient water for 100% by weight, all weights based on the weight of the total composition.

2. A composition of claim 1 containing 1 to 2% by weight of panthenol.

3. A composition of claim 1 containing 1 to 2% by weight of methionine.

4. A composition of claim 1 containing 1 to 2% by weight of carraghenate.

5. A composition of claim 1 containing about 0.9% by weight of sodium chloride.

6. A composition of claim 1 containing 0.1 to 2% by weight of a preservative which is at least one member of the group consisting of phenylglycol, methyl p-hydroxy-benzoate and propyl p-hydroxy-benzoate.

7. A composition of claim 6 containing 0.2% by weight of methyl p-hydroxy-benzoate.

8. A composition of claim 6 containing 0.1% by weight of propyl p-hydroxy-benzoate.

9. A composition of claim 1 containing at least one member of the group consisting of 0.1 to 0.5% by weight of perfume and 0.01 to 0.3% by weight of an antioxidant.

10. A method of treating sun eczema and dyshidrosis of the skin comprising applying to the skin an amount of a composition of claim 1 sufficient to treat sun eczema and dyshidrosis.

11. The method of claim 10 wherein the skin has been previously cleaned.

12. The method of claim 10 wherein the application is made to 6 times per day.

13. A method of claim 10 wherein the composition contains 1 to 2% by weight of panthenol.

14. The method of claim 10 wherein the composition contains 1 to 2% by weight of methionine.

15. A method of claim 10 wherein the composition contains 1 to 2% by weight of carraghenate.

16. The method of claim 10 wherein the composition contains about 0.9% by weight of sodium chloride.

17. A method of claim 10 wherein the composition contains 0.1 0.1 to 2% by weight of a preservative which is at least one member of the group consisting of phenylglycol, methyl p-hydroxy-benzoate and propyl p-hydroxy-benzoate.

18. A method of claim 17 wherein the composition contains 0.2% by weight of methyl p-hydroxy-benzoate.

19. A method of claim 17 wherein the composition contains 0.1% by weight of propyl p-hydroxy-benzoate.

20. A method of claim 10 wherein the composition contains at least one member of the group consisting of 0.1 to 0.5% by weight of perfume and 0.01 to 0.3% by weight of an antioxidant.

* * * * *